US007489825B2

(12) United States Patent
Sirohey et al.

(10) Patent No.: US 7,489,825 B2
(45) Date of Patent: Feb. 10, 2009

(54) METHOD AND APPARATUS FOR CREATING A MULTI-RESOLUTION FRAMEWORK FOR IMPROVING MEDICAL IMAGING WORKFLOW

(75) Inventors: Saad Ahmed Sirohey, Pewaukee, WI (US); Gopal B. Avinash, New Berlin, WI (US)

(73) Assignee: GE Medical Systems, Schenectady, NY (US)

( * ) Notice: Subject to any disclaimer, the term of this patent is extended or adjusted under 35 U.S.C. 154(b) by 620 days.

(21) Appl. No.: 11/180,270

(22) Filed: Jul. 13, 2005

(65) Prior Publication Data

US 2007/0014480 A1 Jan. 18, 2007

(51) Int. Cl.
*G06K 9/36* (2006.01)

(52) U.S. Cl. ...................................................... 382/244

(58) Field of Classification Search ................. 382/128, 382/131, 232–233, 240, 248, 299, 302; 348/395.1, 348/400.1, 403.1, 408.1; 375/240.18–240.19; 378/4, 21, 23, 62; 128/920, 922, 923; 708/400, 708/401
See application file for complete search history.

(56) References Cited

U.S. PATENT DOCUMENTS

| | | | | |
|---|---|---|---|---|
| 6,173,083 | B1 | 1/2001 | Avinash | |
| 6,208,763 | B1 | 3/2001 | Avinash | |
| 6,343,936 | B1 * | 2/2002 | Kaufman et al. | 434/262 |
| 6,782,137 | B1 | 8/2004 | Avinash | |
| 6,912,319 | B1 * | 6/2005 | Barnes et al. | 382/240 |
| 6,987,831 | B2 * | 1/2006 | Ning | 378/37 |
| 7,020,314 | B1 * | 3/2006 | Suri et al. | 382/130 |
| 7,327,866 | B2 * | 2/2008 | Bae et al. | 382/131 |
| 7,376,279 | B2 * | 5/2008 | Dekel et al. | 382/240 |
| 2002/0044696 | A1 | 4/2002 | Sirohey et al. | |
| 2002/0057844 | A1 | 5/2002 | Sirohey et al. | |
| 2002/0057850 | A1 | 5/2002 | Sirohey et al. | |

OTHER PUBLICATIONS

Lossless Image Compression Using Integer to Integer Wavelet Transforms; A.R. Calderbank†, Ingrid Daubechies‡, Wim Sweldens*, Boon-Lock Yeo**; AT&T-Labs Research, 180 Park Ave Bldg 103, Florham Park, NJ 07932; Program for Applied and Computational Methematics, Princeton University, Princeton, NJ 08544; Lucent Technologies, Bell Laboratories, Rm. 2C-175, 700 Mountain Avenue. Murray Hill NJ 07974; IBM Thomas J. Watson Research Center, PO Box 704, Yorktown Heights, NY 10598.

* cited by examiner

*Primary Examiner*—Jose L Couso
(74) *Attorney, Agent, or Firm*—The Small Patent Law Group; Dean D. Small

(57) ABSTRACT

Method and apparatus for handling data comprises decomposing data into a plurality of resolution levels using an integer wavelet decomposition. A transform module may be used to perform forward and inverse transformations on multi-dimensional data using integer wavelet transforms. A data stream is compiled comprising the plurality of resolution levels in a predetermined order. At least one resolution level of the plurality of resolution levels associated with a workflow application is accessed by a processor, and the workflow application is performed on the at least one resolution level.

29 Claims, 10 Drawing Sheets

Forward Transform:

Inverse Transform:

110 — LLL | LHL / HLL | HHL ; LLH | LHH / HLH | HHH

↓ Intermediate Results after Transformation in Y

112 — LL$_U$ | HL$_U$ / LL$_L$ | HL$_L$ ; LH$_U$ | HH$_U$ / LH$_L$ | HH$_L$ $LL_U = LLL + \lfloor(HLL+1)/2\rfloor$;  $LL_L = LL_U - HLL$;
$HL_U = LHL + \lfloor(HHL+1)/2\rfloor$;  $HL_L = HL_U - HHL$;
$LH_U = LLH + \lfloor(HLH+1)/2\rfloor$;  $LH_L = LH_U - HLH$;
$HH_U = LHH + \lfloor(HHH+1)/2\rfloor$;  $HH_L = HH_U - HHH$.

↓ Intermediate Results after Transformation in X

114 — $L_1$ | $H_1$ / $L_3$ | $H_3$ ; $L_2$ | $H_2$ / $L_4$ | $H_4$ $L_1 = LL_U + \lfloor(HL_U+1)/2\rfloor$;  $L_2 = L_1 - HL_U$;
$L_3 = LL_L + \lfloor(HL_L+1)/2\rfloor$;  $L_4 = L_3 - HL_L$;
$H_1 = LH_U + \lfloor(HH_U+1)/2\rfloor$;  $H_2 = H_1 - HH_U$;
$H_3 = LH_L + \lfloor(HH_L+1)/2\rfloor$;  $H_4 = H_3 - HH_L$.

↓ Intermediate Results after Transformation in Z

116 — a | e / c | g ; b | f / d | h $a = L_1 + \lfloor(H_1+1)/2\rfloor$;  $e = a - H_1$;
$c = L_3 + \lfloor(H_3+1)/2\rfloor$;  $g = c - H_3$;
$B = L_2 + \lfloor(H_2+1)/2\rfloor$;  $f = b - H_2$;
$d = L_4 + \lfloor(H_4+1)/2\rfloor$;  $h = d - H_4$.

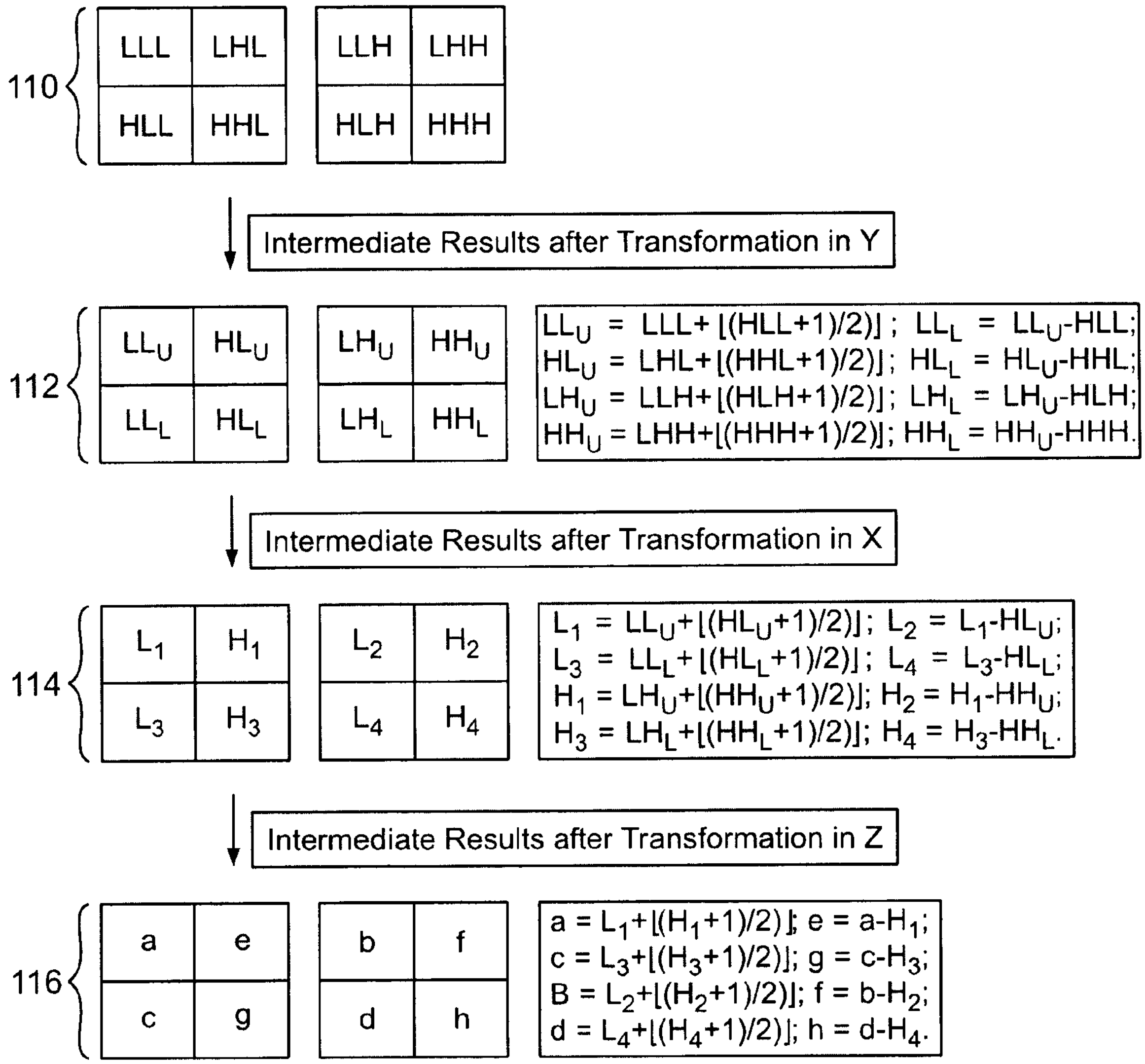

| Functional Domain | | Workflow Applications | | | | |
|---|---|---|---|---|---|---|
| | **Acquisition** 202 | Quick Preview | Quality Control | CAD | Artifact Reduction | Acquisition Speed up (slip ring bandwidth) |
| | **Processing** 212 | Noise Reduction | Artifact Reduction | Image Enhancement | Image Reconstruction | Storage of Unprocessed Data for Future Processing |
| | **Analysis** 224 | CAD | Segmentation | CADx | Pattern Recognition | Registration |
| | **Display** 234 | Volume Rendering | Volume of Interest Rendering | CAD Results Referencing | | |
| | **Archive/ Retrieval** 242 | File Format (3D or Higher) | Compression (3D or Higher) | Region of Interest Access | | |
| | **Connectivity** 248 | DICOM Multiframe | Rearrangement of Data | | | |
| | **Beyond 3D** 254 | Dynamic 3D Motion | Multi-Spectra | Multi-Tracers | Multi-phase | |

FIG. 9

METHOD AND APPARATUS FOR CREATING A MULTI-RESOLUTION FRAMEWORK FOR IMPROVING MEDICAL IMAGING WORKFLOW

BACKGROUND OF THE INVENTION

This invention relates generally to receiving, managing and storing volumes of image data, and more particularly, to storing volumes of image data in a lossless format which is readily consumable by applications.

As medical imaging technology improves, the amount of patient data acquired also increases. Currently, complete datasets representing volumes are stored and transferred. The complete datasets may alternatively be compressed or decimated to conserve storage space and increase the speed of transferring the data, but some of the original information is lost in the compression process. Also, as the amount of image data increases, so does the time necessary to access, process and display the data.

For example, a first application reads a complete dataset, decimates the data to a desired level, and then processes the data. This process is repeated by every subsequent application which accesses the dataset. Thus, when new views are desired, the process of decimating the data is repeated. Also, data may be processed at a level the display cannot support, which is a waste of time and processing power.

In addition, when transferring data, such as from an acquisition system to a remote viewing and processing station, the entire dataset is transferred. This is time consuming and requires a large amount of bandwidth and storage at the processing station.

Therefore, a need exists for a more efficient manner in which to store and manage volumes of data. Certain embodiments of the present invention are intended to meet these needs and other objectives that will become apparent from the description and drawings set forth below.

BRIEF DESCRIPTION OF THE INVENTION

In one embodiment, a method for handling data comprises decomposing data into a plurality of resolution levels using an integer wavelet decomposition. A data stream is compiled comprising the plurality of resolution levels in a predetermined order. At least one resolution level of the plurality of resolution levels associated with a workflow application is accessed, and the workflow application is performed on the at least one resolution level.

In another embodiment, a system for handling image data comprises a transform module for performing forward and inverse transformations on multi-dimensional data using integer wavelet transforms. The forward transformation produces a plurality of resolution levels. A processor compiles a data stream comprising the plurality of resolution levels in a predetermined order, and a memory stores the data stream. The processor accesses at least one resolution level of the plurality of resolution levels based on a workflow application.

In another embodiment, a method for forming a multi-resolution framework of data comprises decomposing data into multiple resolution levels using an integer wavelet decomposition. The data comprises at least three dimensions, and each of the resolution levels comprises data blocks representative of a volume of data. A data stream is compiled comprising the data blocks arranged in an order based on the resolution level. A first set of data blocks within the data stream is accessed at a predetermined resolution level which is associated with a workflow application. The workflow application is performed on the first set of data blocks.

BRIEF DESCRIPTION OF THE DRAWINGS

FIG. 5 illustrates an inverse transform process in accordance with an embodiment of the present invention.

FIG. 9 illustrates a matrix of workflow applications which benefit from using data processed and saved using the IWMR framework in accordance with an embodiment of the present invention.

The foregoing summary, as well as the following detailed description of certain embodiments of the present invention, will be better understood when read in conjunction with the appended drawings. It should be understood that the present invention is not limited to the arrangements and instrumentality shown in the attached drawings.

DETAILED DESCRIPTION OF THE INVENTION

Figure 1:
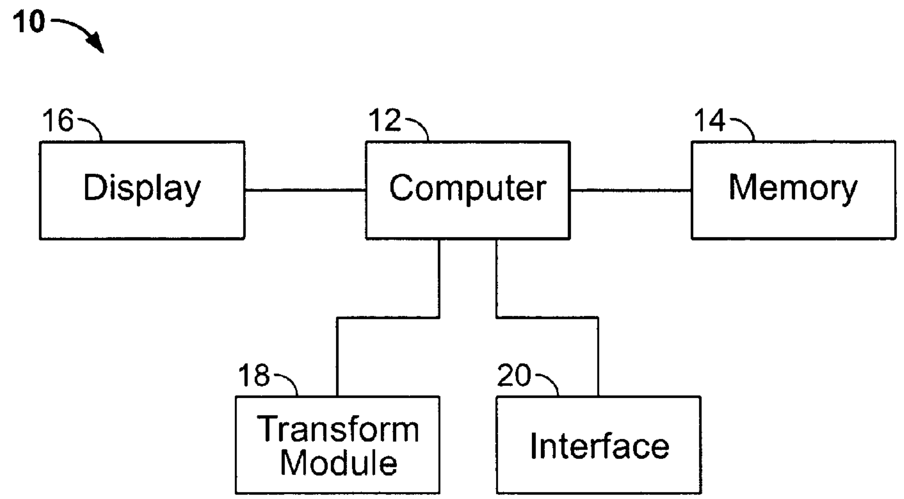
FIG. 1 illustrates a block diagram of a computer system in accordance with an embodiment of the present invention.

FIG. 1 illustrates a block diagram of a computer system 10 in accordance with an embodiment of the present invention. By way of example only, the computer system 10 may be a PACS or other processing station. The computer system 10 comprises components such as a computer 12 which is interconnected with a memory 14 and display 16. The computer 12 communicates via an input/output interface 20 to share information and data with other computers, processing stations, and data acquisition systems, such as medical diagnostic systems. The interface 20 may be interconnected with, for example, a LAN, WAN or the internet. A transform module 18 may be formed integral with or interconnected to the computer 12. The transform module 18 performs forward and/or inverse integer wavelet transformations on datasets to form multi-resolution datasets. The multi-resolution datasets are ordered and stored in a data stream as discussed below, forming an integer wavelet multi-resolution (IWMR) framework which may be stored in the memory 14. A desired level of the multi-resolution dataset may be accessed and processed by the computer 12, then output on the display 16.

Figure 2:
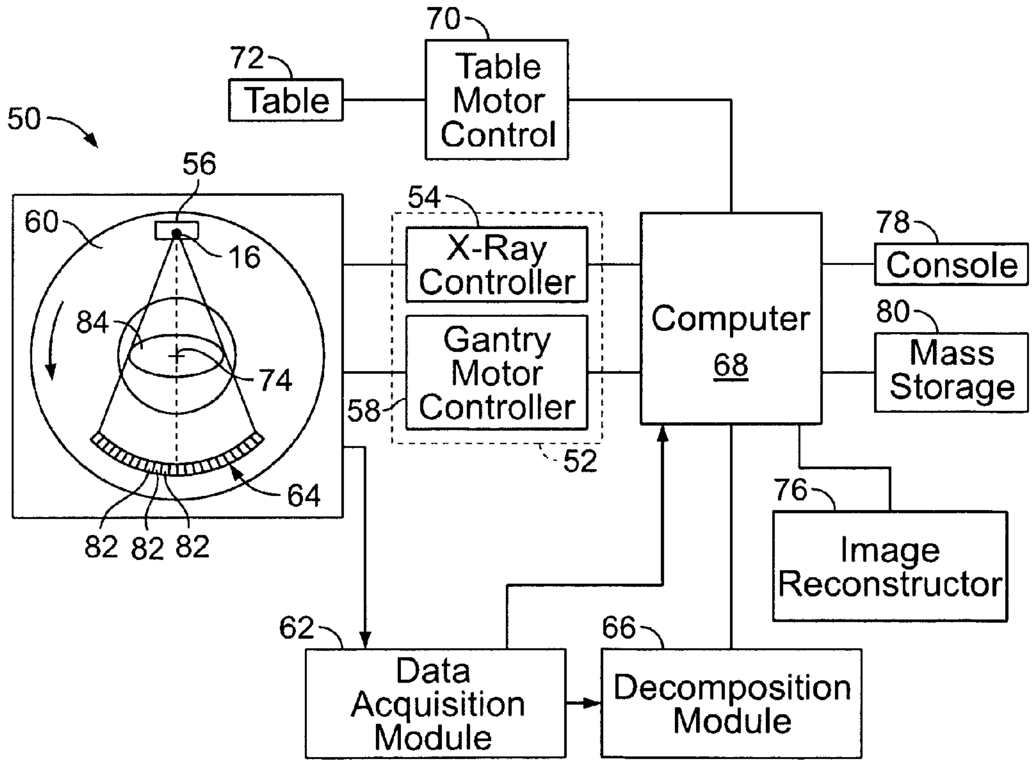
FIG. 2 illustrates a block diagram of a CT imaging system in accordance with an embodiment of the present invention.

FIG. 2 illustrates a block diagram of a CT imaging system 50 in accordance with an embodiment of the present invention. It should be understood that the CT imaging system 50 is provided as an example only, and that other data acquisition systems, such as MRI, Ultrasound and Nuclear Medicine may also be used. The control subsystem of the CT imaging system 50 has gantry associated control modules 52 which include: x-ray controller 54, which provides power and timing signals to an x-ray source 56, and gantry motor controller 58, which controls the rotational speed and position of the gantry 60. A data acquisition module 62 receives projection data from a detector array 64 and converts the data into digital form for later computer processing. A decomposition module 66 may receive the data from the data acquisition module 62 or computer 68 and use an integer wavelet transformation to decompose the data into multi-resolution datasets as discussed further below. The x-ray controller 54, the gantry motor controller 58, the data acquisition module 62, and the decomposition module 66 are connected to the computer 68. It should be understood that the functionality of the decomposition module 66 may be accomplished by the computer 68.

The computer 68 also governs operation of a table motor control 70 which drives a motor that moves a patient table 72 along the z-axis 74. The computer 68 may be connected to an image reconstructor 76 which performs high speed image reconstruction according to methods known in the art.

The computer 68 receives commands and scanning parameters via an operator console 78 which is generally a CRT display and keyboard that enables an operator to enter parameters for the CT scan and to display the reconstructed image. A mass storage device 80 provides a means for storing operating programs.

During data acquisition, the CT imaging system 50 may function as a conventional cone-beam system in gathering data. In a step-and-shoot acquisition method, the table 72 is held stationary as the x-ray source 56 and detector array 64 make a complete revolution around the gantry 60 about the z-axis 74, located within a patient 84. At each of a plurality of angular positions, the attenuation data from detectors 82 comprising the detector array 64 are received by the data acquisition module 62. Upon completion of a full rotation, the computer 68 commands the table motor control 70 to advance the table 72 to another position along the z-axis 74 and another rotational scan of the patient 84 is performed. This process is repeated until the desired portion of the patient 84 has been fully scanned. Alternatively, the CT imaging system 50 may acquire data in the helical acquisition mode, wherein the table motor control 70 advances the table 72 as the x-ray source 56 and detector array 64 are rotated and scan data is acquired. In the helical acquisition mode, the scan data is transferred via slip ring technology. The decomposition module 66 decomposes the three-dimensional scan data into a plurality of resolution levels using the integer wavelet decomposition.

Figure 3:
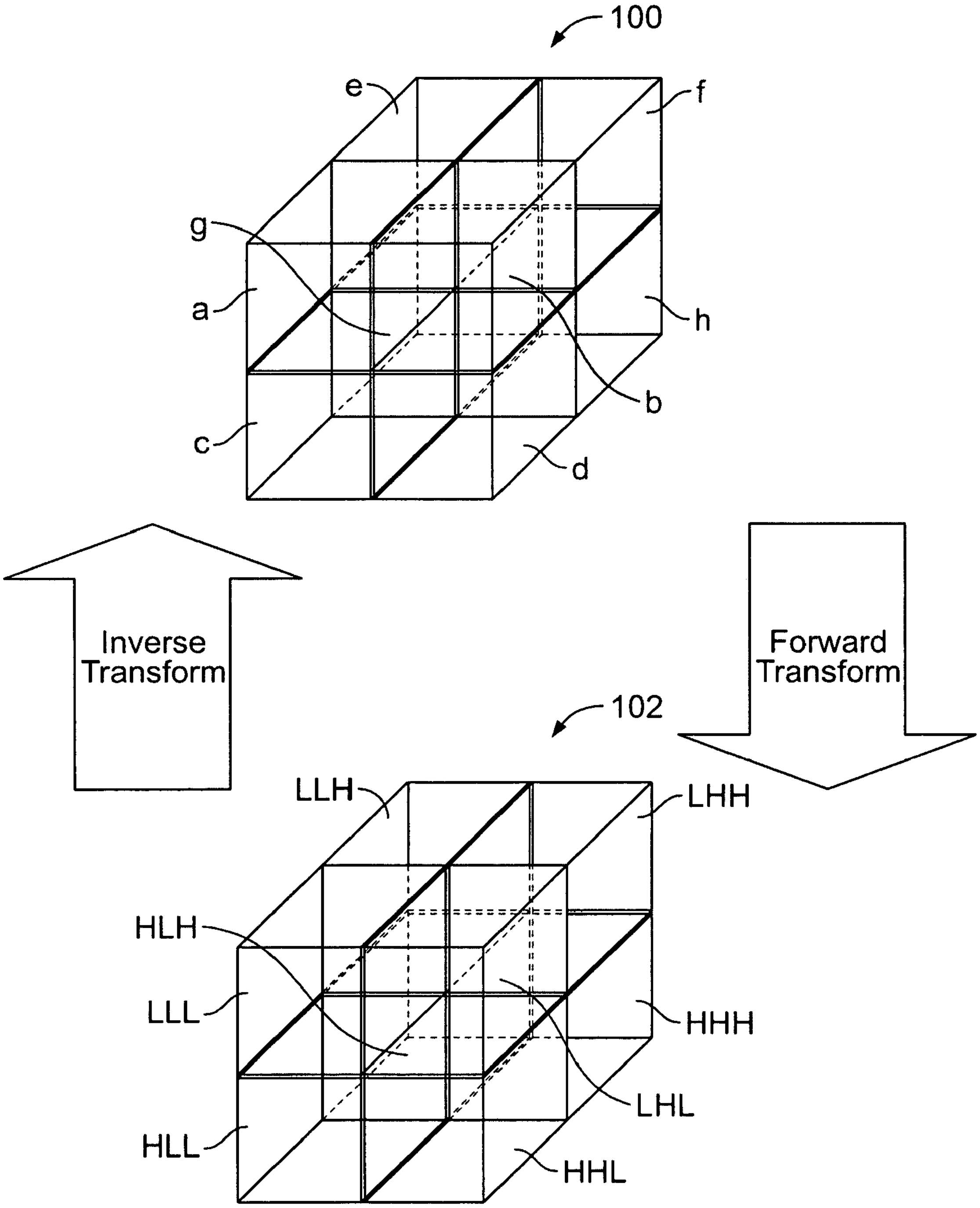
FIG. 3 illustrates a volume of data formed in accordance with an embodiment of the present invention.

FIG. 3 illustrates a volume 100 of data formed in accordance with an embodiment of the present invention. The volume 100 is representative only. It should be understood that the data, such as image data, may be stored as a series of values representative of voxels in data blocks. The volume 100 is logically divided into eight subsets of data, indicated by letters a-h. If the volume 100 comprises image data, each subset a-h of data represents a portion of an object of interest, such as a portion of the patient 84.

Integer wavelet decomposition involves a dyadic filtering and sub-sampling process which creates a hierarchical set of sub-bands. A single level decomposition results in one low frequency sub-band along with three high frequency sub-bands. Typically, wavelet transforms are real (floating point) filters with the result also being real values. Until recently only the S-Transform (a modified Haar wavelet) provided an integer based transformation and reconstruction. As evident from the nature of the transformation it is very difficult to preserve precision with floating point operations. Recently, a technique called "lifting" was proposed by Calderbank et al. which could be employed to any wavelet transformation to make it an integer based transformation with full reversibility.

A one step forward wavelet transform in one dimension is based on the following equations:

$$L(n)=\lfloor (C(2n)+C(2n+1))/2 \rfloor, \text{ for } n \in [0,N/2-1]; \text{ and}$$

$$H(n)=C(2n)-C(2n+1),$$

where C(i) for i ∈ [0, N−1−] represents the input data, L and H are the decomposed low and high frequency components and C is the input data. The "⌊ . . . ⌋" operation produces the greatest integer less than the operands with "N" being the size of the input data. The converse of the one step forward wavelet transform is the one step inverse wavelet transform, which is described by the following equations:

$$C(2n)=L(n)+\lfloor (H(n)+1)/2 \rfloor; \text{ and}$$

$$C(2n+1)=C(2n)-H(n).$$

An implicit assumption in the equations above is that the data size "n" is even. Though valid for theoretical analysis and description, this assumption does not satisfy the myriad of data sets that are encountered in reality. Therefore, taking care of the odd and even sizes of the input data is addressed along with extending the one-dimensional transform to a two-dimensional (2D) transform.

The equations for the forward and inverse wavelet transforms described above are for a one-dimensional single step transformation. A recursion of a single step wavelet transform is performed on the "LL" component at every level. The number of levels for the transformation is determined by fixing the row and/or column size of the smallest resolution. This level value is determined by the steps necessary to decompose the maximum of the row or column size of the original image to the desired smallest resolution size. If "n" is this level variable then the following equation is used:

$$n=\log_2(\max(\text{rows},\text{cols}))-\log_2(d_{size}),$$

where "n" is the number of levels of decomposition, rows and columns are the original image dimensions, $\log_2$ is the log in base 2, and $d_{size}$ is the configurable size of the smallest resolution image.

Special handling of the odd row or column at every level is performed. The odd row or the odd column is replicated with the aim to force it to be even so that the algorithm for the wavelet transformation is a seamless unit. This addition adds to the size of the image storage, however, the additions are negligible when compression is performed because the high frequency sub-bands will have all zeros in those rows or columns.

The 2D forward transformation is governed by the following equations:

$$ll=\lfloor (\lfloor (a+b)/2) \rfloor + \lfloor (c+d)/2 \rfloor)/2 \rfloor;$$

$$hl=\lfloor ((a-b)+(c-d))/2 \rfloor;$$

$$lh=\lfloor (a+b)/2 \rfloor - \lfloor (c+d)/2 \rfloor; \text{ and}$$

$$hh=(a-b)-(c-d).$$

The inverse transform process works by taking the smallest resolution "LL" band and combining it with its associated "HL", "LH" and "HH" bands to produce the next higher resolution. This process is repeated until either the full resolution of the image is achieved or a specified level of resolution is attained.

The 2D inverse transform is governed by the following set of equations:

$$a=ll+\lfloor(hl+1)/2\rfloor+\lfloor(lh+\lfloor(hh+1)/2\rfloor)+1)/2\rfloor;$$

$$b=ll+\lfloor(hl+1)/2\rfloor+\lfloor((lh+\lfloor(hh+1)/2\rfloor)+1)/2\rfloor-(lh+\lfloor(hh+1)/2\rfloor);$$

$$c=ll+\lfloor(hl+1)/2\rfloor-hl+\lfloor(lh+\lfloor(hh+1)/2\rfloor-hh+1)/2\rfloor; \text{ and}$$

$$d=(ll+\lfloor(hl+1)/2\rfloor-hl+\lfloor(lh+\lfloor(hh+1)/2\rfloor)-((lh+\lfloor(hh+1)/2\rfloor)-hh).$$

The inverse transform is modular with respect to single level reconstruction, allowing users to specify a desired level, from the smallest resolution to full resolution, for reconstruction.

Figure 4:
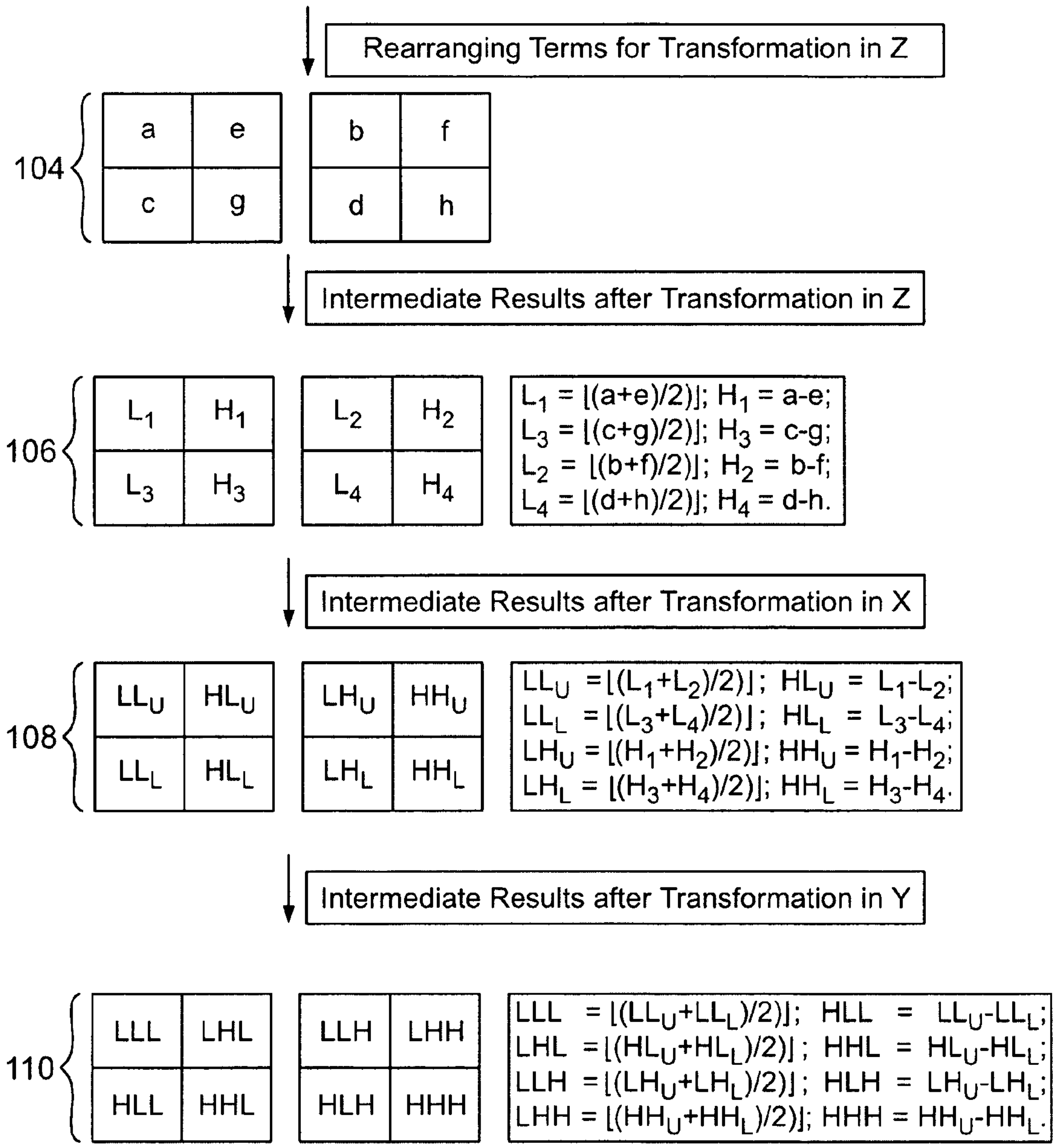
FIG. 4 illustrates a forward transform process using integer wavelet decomposition in accordance with an embodiment of the present invention.

FIG. 4 illustrates a three-dimensional (3D) forward transform process using integer wavelet decomposition in accordance with an embodiment of the present invention. The transformation may be performed in any order as long as the forward and inverse transformations are performed in the reverse order with respect to each other. For example, the transform module 18 or the decomposition module 66 perform the forward transform process on the volume 100 in FIG. 3 in the Z, X and then Y dimensions using an integer wavelet transform process, resulting in a first level transformation 102 (FIG. 3). Input data 104 is a representation of the eight subsets of data a-h of the volume 100. The three-dimensional transform in the Z dimension, operating on the input data 104 and resulting in intermediate results 106, may be accomplished by the following equations:

$$L_1=\lfloor(a+e)/2)\rfloor;$$

$$H_1=a-e;$$

$$L_3=\lfloor(c+g)/2)\rfloor;$$

$$H_3=c-g;$$

$$L_2=\lfloor(b+f)/2)\rfloor;$$

$$H_2=b-f;$$

$$L_4=\lfloor(d+h)/2)\rfloor; \text{ and}$$

$$H_4=d-h.$$

The 3D transform in the X dimension, operating on the intermediate results 106 and resulting in intermediate results 108, may be accomplished by the following equations:

$$LL_U=\lfloor(L_1+L_2)/2)\rfloor;$$

$$HL_U=L_1-L_2;$$

$$LL_L=\lfloor(L_3+L_4)/2)\rfloor;$$

$$HL_L=L_3-L_4;$$

$$LH_U=\lfloor(H_1+H_2)/2)\rfloor;$$

$$HH_U=H_1-H_2;$$

$$LH_L=\lfloor(H_3+H_4)/2)\rfloor; \text{ and}$$

$$HH_L=H_3-H_4.$$

The 3 D transform in the Y dimension, operating on the intermediate results 108 and resulting in intermediate results 110, may be accomplished by the following equations:

$$LLL=\lfloor(LL_U+LL_L)/2)\rfloor;$$

$$HLL=LL_U-LL_L;$$

$$LHL=\lfloor(HL_U+HL_L)/2)\rfloor;$$

$$HHL=HL_U-HL_L;$$

$$LLH=\lfloor(LH_U+LH_L)/2)\rfloor;$$

$$HLH=LH_U-LH_L;$$

$$LHH=\lfloor(HH_U+HH_L)/2)\rfloor; \text{ and}$$

$$HHH=HH_U-HH_L.$$

Intermediate results 110 represent a first level of decomposition (1,1,1), pictorially illustrated as the first level transformation 102 (FIG. 3). The forward transform of FIG. 4 may be repeated for additional levels of decomposition, facilitating the integer wavelet multi-resolution (IWMR) framework. For example, the LLL block may be logically divided into a-h as in the volume 100 of FIG. 3. The decomposition module 66 performs the forward transform on the volume LLL in the Z, X and Y dimensions using the integer wavelet forward transform process, resulting in a second level of decomposition (2,2,2).

FIG. 5 illustrates a 3D inverse transform process in accordance with an embodiment of the present invention. The transformation is in the reverse order with respect to the forward transform. The decomposition module 66 performs the inverse transform in the reverse order with respect to the forward transform, starting with the intermediate results 10 in FIG. 4 in the Y dimension, and then the X and Z dimensions. The 3D transform in the Y dimension, operating on the intermediate results 110 and resulting in intermediate results 112, may be accomplished by the following equations:

$$LLU=LLL+\lfloor(HLL+1)/2)\rfloor;$$

$$LLL=LLU-HLL;$$

$$HLU=LHL+\lfloor(HHL+1)/2)\rfloor;$$

$$HLL=HLU-HHL;$$

$$LHU=LLH+\lfloor(HLH+1)/2)\rfloor;$$

$$LHL=LHU-HLH;$$

$$HHU=LHH+\lfloor(HHH+1)/2)\rfloor; \text{ and}$$

$$HHL=HHU-HHH.$$

The 3D inverse transform in the X dimension, operating on the intermediate results 112 and resulting in intermediate results 114, may be accomplished by the following equations:

$$L1=LLU+\lfloor(HLU+1)/2)\rfloor;$$

$$L2=L1-HLU;$$

$$L3=LLL\lfloor(HLL+1)/2)\rfloor;$$

$$L4=L3-HLL;$$

$$H1=LHU+\lfloor(HHU+1)/2)\rfloor;$$

$$H2=H1-HHU;$$

$$H3=LHL+\lfloor (HHL+1)/2)\rfloor; \text{ and}$$

$$H4=H3-HHL.$$

The 3D inverse transform in the Z dimension, operating on the intermediate results 114 and resulting in the intermediate results 116, which are equivalent to the input data 104 of FIG. 4, may be accomplished by the following equations:

$$a=L1+\lfloor (H1+1)/2)\rfloor;$$

$$e=a-H1;$$

$$c=L3+\lfloor (H3+1)/2)\rfloor;$$

$$g=c-H3;$$

$$b=L2+\lfloor (H2+1)/2)\rfloor;$$

$$f=b-H2;$$

$$d=L4+\lfloor (H4+1)/2)\rfloor; \text{ and}$$

$$h=d-H4.$$

Figure 6:
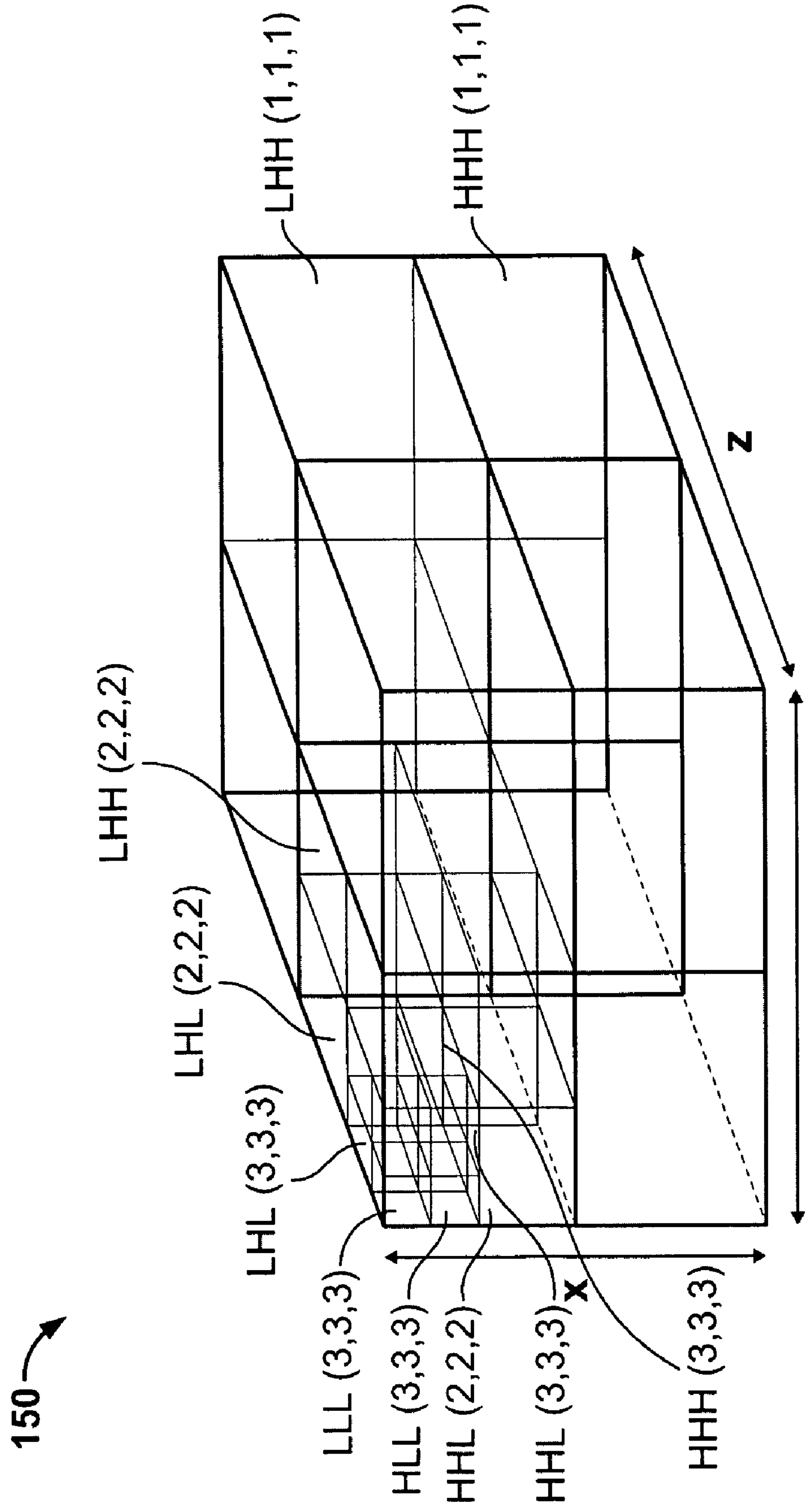
FIG. 6 illustrates the reorganization of data for a multi-level decomposition of a three-dimensional volumetric dataset using IWMR in accordance with an embodiment of the present invention.

FIG. 6 illustrates the reorganization of data for a multi-level decomposition of a 3D volumetric dataset using IWMR in accordance with an embodiment of the present invention. A plurality of resolution levels 150 is illustrated. By way of example only, the volume 100 may be organized into a multi-resolution framework having three levels of decomposition where the size of the smallest low frequency component is $$\left(\frac{x}{2^n}, \frac{y}{2^m}, \frac{z}{2^k}\right),$$

where x, y, and z are the original size of the data and n, m, and k are the levels of the dyadic decompositions in each dimension. In this example, n=m=k=3, meaning that the volumetric dataset has been decomposed to the same number of levels in all dimensions.

In this example, the volume 100 was decomposed using the equations of FIG. 4 to form the first level of decomposition (1,1,1). Similarly, the subset LLL(1,1,1) was decomposed to form a second level of decomposition (2,2,2), and then the subset LLL(2,2,2) was decomposed, resulting in the third level of decomposition (3,3,3). Not all of the subsets in FIG. 6 are illustrated for clarity.

The technical effect is that the multi-resolution framework of FIG. 6 provides a solution to the problem of managing very large amounts of data and utilizes the complete reversibility of the integer wavelet as the basic building block. The dimension separability and modular nature of the integer wavelet transformation allows the extension of the framework to any number of dimensions. Also, the framework allows the reordering of any multi-dimensional data into a multi-resolution framework.

The following example uses a typical set of dimensions of a CT exam where x=512, y=512 and z=2048 (using 2048 for simplicity in dyadic calculations). If a volumetric rendering of the whole volume is one of the tasks of an application, then for a two 16 bit value the RAM needed is 512*512*2048*2=1 GB. Typically it is not possible to display the whole volume for reasons of efficiency and speed (as well as available visual space on the display device). Therefore, tasks such as decimation are used to reduce the data and then display a reduced image of the whole volume. Alternatively, if the data is already in a reduced form, such as a 2 level decomposition, then the data needed for visualization is only 512/4*512/4*2048/4 *2=128*128*512*2=16 MB. This is effectively a reduction of 2 orders of magnitude compared to the original 1 GB data. It should be understood that the data is only reordered and the full 512×512×2048 CT exam data is always available because of the complete reversibility of the integer wavelet transform.

In addition, an anisotropic volume of data may be transformed or decomposed as described above. In general, higher sampled dimensions may be decomposed until a ratio of anisotropy for the lower sampled dimensions reaches less than or equal to 1.5. For example, a volume may have the voxel dimensions of 1:1:5; being isotropic in the X and Y dimensions and anisotropic in the Z dimension. A first decomposition is performed in the X and Y dimensions, resulting in the voxel ratios becoming 2:2:5. A second decomposition is performed in the X and Y dimensions, forming the voxel ratios 4:4:5. A third decomposition, and subsequent decompositions, would be performed in the same manner as an isotropic volume, maintaining the ratio of 1:1:1.25.

Figure 7:
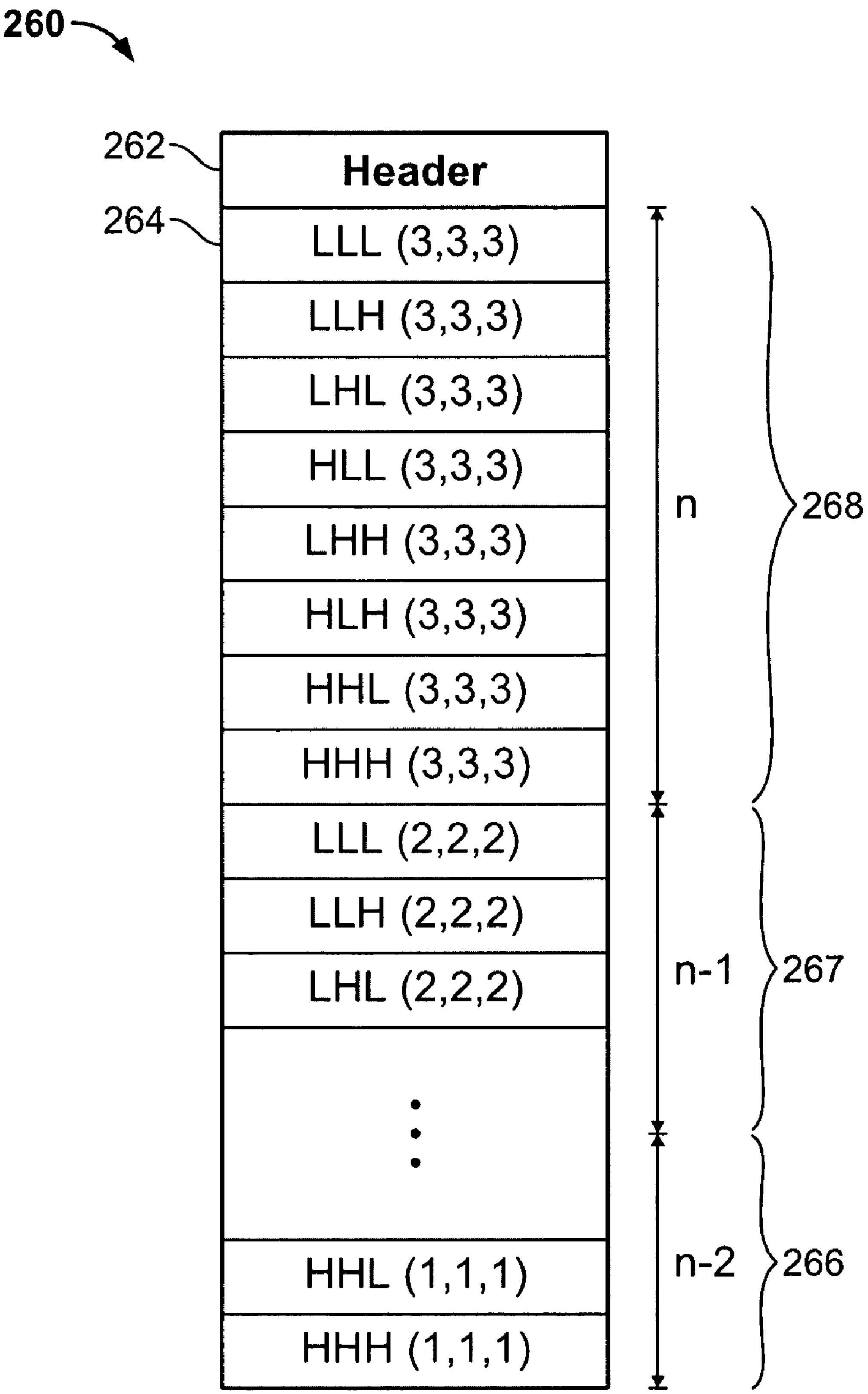
FIG. 7 illustrates a data stream comprising three multi-resolution levels in accordance with an embodiment of the present invention.

FIG. 7 illustrates a data stream 260 comprising three multi-resolution levels in accordance with an embodiment of the present invention. The smallest resolution n, third resolution level 268, in this example (3,3,3), is first within the data stream 260, followed by the n-1, second resolution level 267, or (2,2,2), followed by the n-2, first resolution level 266, or (1,1,1). As illustrated, a first data block 264 starts with the LLL(3,3,3) block. Therefore, the data is stored as volume blocks of data which are concatenated with one another to form a multi-resolution data stream, progressively getting to full resolution.

By way of example, the data stream 260 may be ordered to maintain the methodology or format of the DICOM multi-frame format, in which one global file header is used, followed by the data from the multiple images in raw data format. For example, after the file header, the first data element of the file may be the first voxel of the first slice, row ordered to the last voxel of the first slice. The first voxel of the second slice is then concatenated with the last voxel of the first slice, the second slice is row ordered to the last voxel of the second slice, and so on.

Referring also to FIG. 6, the data stream 260 may be formed by a combination of the DICOM multi-frame format and IWMR. A header 262 comprises information about each volume block of data. The header 262 may contain information such as the version of the multi-resolution scheme, the type of forward transform, the number of levels of wavelet decomposition, the row and column values of every sub-band level (resolution), and the compressed sizes of all the sub-bands from smallest to the largest.

Therefore, a volume in real space, such as LLL(3,3,3) of FIG. 6, is composed of a subset of data blocks from a multi-resolution framework of the volume, such as volume 100 of FIG. 3. To reconstruct a specific volume of interest, only a portion of the data blocks, rather than all of the data blocks, needs to be accessed. The portion depends upon the intended purpose, such as the desired resolution level defined by the processing algorithm, the resolution capability of the display, or a defined ROI. Therefore, the data may be "packed" and "unpacked" faster than data stored only in the DICOM multi-frame format. Also, only the data of the desired resolution needs to be accessed, rather than accessing the data at full resolution and then decimating the data or processing all of the data when not desired or necessary, which requires an increasing amount of time and processing power. With the IWMF framework, it is easy to display and/or access a scaled version of the image data the user wants. Therefore, when the user selects an image to be displayed, the system displays a scaled version based on the display capability. Even while the data is being acquired, a scaled version may be displayed. No data is lost, however, as is experienced with previous methods of compression.

Figure 8:
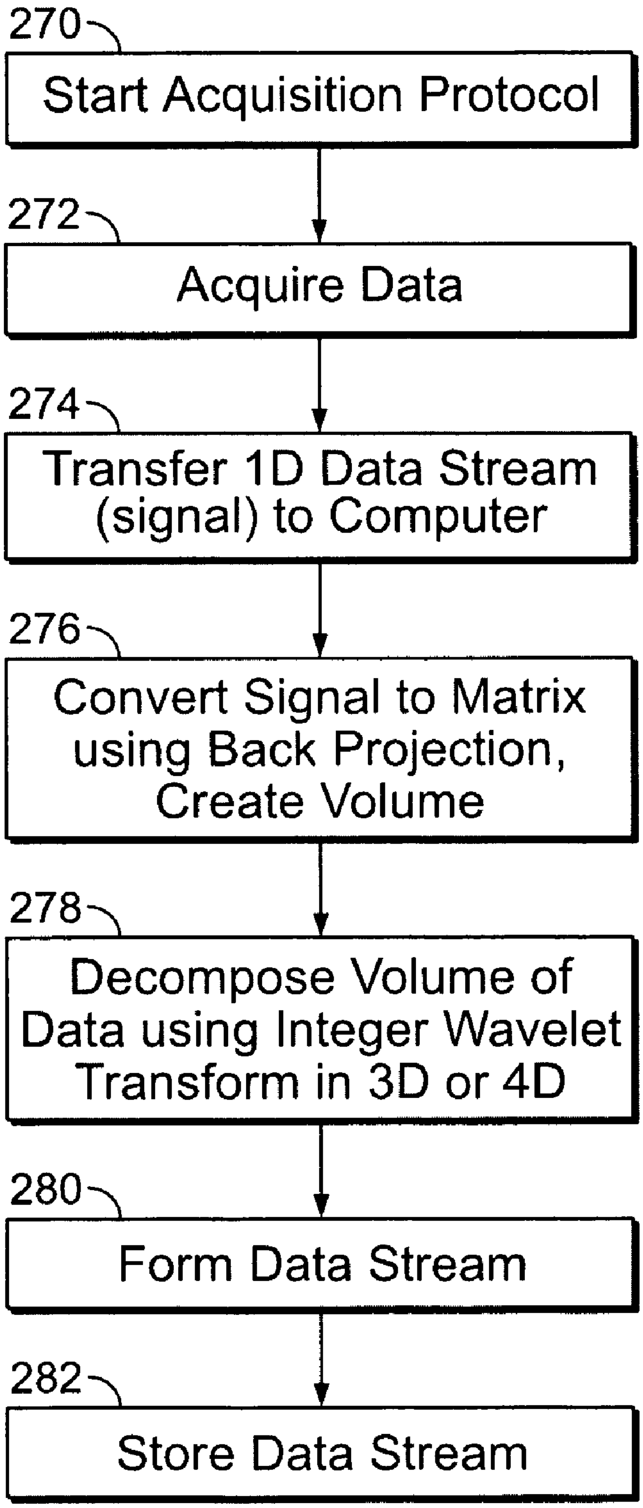
FIG. 8 illustrates a flow chart of a method using integer wavelet decomposition in accordance with an embodiment of the present invention.

FIG. 8 illustrates a flow chart of a method using integer wavelet decomposition in accordance with an embodiment of the present invention. In step 270, an acquisition protocol is started. It should be understood that many different protocols may be used, such as to acquire data with regards to specific anatomy or function within the body. In FIG. 8, a CT scanner, such as the CT imaging system 50, will be used as an example, but it should be understood that a different data acquisition system may be used, and that the data is not limited to image data.

In step 272, data is acquired by the data acquisition module 62. By way of example only, the image data may be acquired as voxels to form slices by a helical or spiral CT scan, having three dimensions, such as X, Y, and Z. Additionally, a fourth dimension of time and a fifth dimension of intensity and/or function, such as a rate of change of contrast, may be acquired. Optionally, the data may be or include non-image data, such as ECG or other patient monitoring data.

In step 274, the data is transferred in a one-dimensional (ID) datastream, such as a sinograph, to the computer 68. Optionally, the data may flow to the decomposition module 66.

In step 276, the data signal may be converted to a matrix using back projection to create a volume of data. In step 278, the volume of data is decomposed using the forward integer wavelet transform in 3D, 4D, or, in general n-dimensional (nD), as appropriate, by the decomposition module 66. Optionally, steps 276 and 278 may be completed fully or partially prior to step 274, reducing the bandwidth of the signal to allow more data to flow through the CT slip rings within a period of time as discussed further below with Acquisition Speed Up.

In step 280, the computer 68 forms the data stream 260, including the header 262. In step 282, the data stream 260 is stored, such as in mass storage device 80 and/or transferred to another computer or processing station, such as the computer system 10. Therefore, the desired subsets of the data stream 260, such as the data corresponding to an ROI at a specific sub-resolution level, may be accessed directly.

FIG. 9 illustrates a matrix 200 of workflow applications which benefit from using data processed and saved using the IWMR framework in accordance with an embodiment of the present invention. The matrix 200 is divided into different functional domains, such as Acquisition 202, Processing 212, Analysis 224, Display 234, Archive/Retrieval 242, Connectivity 248, and Beyond 3D 254. The functional domain Beyond 3D 254 comprises workflow applications having one or more dimensions beyond X, Y and Z, such as temporal and multi-energy situation. It should be understood that the matrix 200 does not limit the use of the multi-resolution level data to the functional domains and workflow applications indicated, but rather, the matrix 200 serves as an illustration of exemplary workflow applications which may be used.

Decomposing data into multi-resolution levels supports the concept of scale space, wherein a dataset at different scales (or resolution levels) can provide different information. Depending upon the intended purpose, a Technologist may want to operate in different scales for zooming in or out. Previously, the processing was done with decimation, which does not give a scaled space concept and is simply data reduction. IWMR is not data reduction, but rather provides the user with data at the correct, desired scale. Therefore, data is reduced only in terms of what is displayed, not the data that is operated on.

Within the functional domain of Acquisition 202, Quick Preview, Quality Control, Computer-Aided Detection (CAD), Artifact Reduction and Acquisition Speed Up are all examples of Workflow Applications. Typically, an acquisition system employs various processing algorithms before a viewable image is obtained. For example, in Computed Radiography (CR) and Digital Radiography (DR), the acquired raw data is processed using various image filtering and enhancement algorithms. In CT, the view (projection space) data is reconstructed into topographic image sets. This processing is a time consuming task for the Quality Assurance/Quality Control Technician due to the latency introduced by the processing time of the algorithms on the, typically, large data sets (2000×2500 pixels) for CR and DR and more than 3000 (each with 512×512 pixels) slices (due to the tremendous increase in the number of slices with improvements in the scanned resolutions, such as Virtual Computed Tomography (VCT)) in CT.

An example of a Quick Preview capability is Ultra Dynamic Range Filtering (UDR), which enhances CR/DR images. On a typical full size CR image, the processing time (memory-to-memory) is about 1.7 sec on a Pentium 3 750 MHz or a Sun Blade UltraSparc III processor based system. However, using data created from the integer wavelet based compression process previously described, the IWMR framework, and applying UDR to the sub-resolution images at a reasonably viewable level on a 21 inch monitor (having approximately 625×512 pixels), the UDR processing is real-time, taking approximately 50 msec, a length of time not measurable by an external timekeeper. Thus, an image with a processed look is displayed that adequately represents the final full scale processed image. For example, a level 3 (313×256 pixels) reconstructed image may be created with and without UDR processing applied. Alternatively, the same anatomical data may be displayed in an image at level 4 (625×512 pixels) with UDR processing using the same parameters.

Sub-resolution IWMR may be used with UDR to enhance CR/DR images, providing a quick preview to the Technologist of what the final (full scale) processed image will look like. UDR processing has the property that the processed look is perceptually similar over a large scale space for the same parameter setting. Other processing techniques may require a mapping of their parameters in the dyadic scale space of the IWMR transformations. A similar extension to the 3D volumetric datasets can be made such that reconstruction algorithms or other filtering methods can be adequately previewed in the sub-resolution IWMR domain.

Quality Control accesses a sub-resolution level to provide an image to the Technologist for quickly verifying the acquisition parameters, the views acquired or being acquired of the patient, and the like. Thus, the data may be checked for quality as it is being acquired or immediately after an acquisition and without waiting for a longer processing time, such as what may be necessary to process a full resolution image or decimate a complete dataset to desired resolution levels.

Computer-Aided Detection (CAD) benefits from IWMF in many different functional domains and will be further discussed below with FIGS. 10-13. Turning to Artifact Reduction, artifacts such as vertical or horizontal structures in the image acquisition process pose a significant challenge to image processing algorithms. To reduce artifacts, the IWMR data may be accessed at different scales, allowing for the artifacts to be easily identified and corrected.

In addition, acquisition systems have a data throughput bottle neck, such as a CT slip ring as discussed previously, which limits the data acquisition speed and time for patient coverage. For Acquisition Speed Up, the IWMF data, together with a lossless compression algorithm (e.g. TruRez), may be used to significantly reduce the bandwidth of the signal or, conversely, allow more data to flow through the slip rings in the same amount of time thereby speeding up the acquisition.

In the Processing 212 functional domain, many types of Workflow Applications benefit from IWMF. Noise Reduction combines the redundancy exploitation of multi-resolution-based techniques with the spatial connectedness of segmentation-based techniques to obtain a robust noise reduction using a computationally efficient implementation. For example, in order to mitigate random noise, many noise reduction filters have been proposed which use multi-resolution decomposition (e.g., wavelet based techniques) to decompose the image into various frequency bands. Each band is processed separately, and then all of the frequency bands are regrouped together to reconstitute the image. This class of techniques has the advantage of modifying a specific spatial frequency band of the image. A well-known corollary of these techniques in image compression is that substantially all the redundancies at a given scale are exploited to achieve high compression ratios without sacrificing the compression quality in these images. Another class of filters is segmentation-based. This class of techniques decomposes the image based on structures and non-structures, processes structures and non-structures separately and then recombines the processed structures and non-structures to form the final filtered image. Unlike in the previous case, this class of methods exploits the spatial connectedness of structures to substantially perform different operations on structures and non-structures.

IWMF also enhances Workflow Applications such as Artifact Reduction, Image Enhancement, and Image Reconstruction during processing. In addition, as the unprocessed data is stored in the IWMF format, the multi-resolution levels are easily accessed in future processing.

Workflow Applications in Analysis 224 enhance the ability of the Technician to analyze the data. Applications include such areas as CAD, Segmentation, CADx, Pattern Recognition and Registration. CAD (computer-aided detection) is the art of detecting features as will be discussed in FIG. 10. CADx is computer-aided diagnosis whereby a necessary decision is made about the feature by classifying it into one of potentially many different categories, such as malignant or benign, for example. Segmentation, Pattern Recognition and Registration are discussed below with CAD in further detail.

Workflow Applications in Display 234 comprise Volume Rendering, Volume of Interest (VOI) rendering, and CAD results referencing. The term volume rendering is used to describe techniques which allow the visualization of three-dimensional data. Volume rendering is a technique for visualizing sampled functions of three spatial dimensions by computing 2D projections of a semitransparent volume. With CAD results referencing, IWMF allows the access of sub-resolution datasets that can be used to display findings of a CAD algorithm without having to perform additional processing.

Large volume datasets impose processing and memory constraints on the volume-rendering engine, making it harder to have an interactive user experience with the rendered datasets. One prior art method for achieving usable interactivity involves volume decimation that consistently eliminates data elements and uses a time delayed full resolution to display the full rendered view. This is undesirable as not all available data is being used, and the data has to be decimated each time the application is run. In contrast, the IWMF format allows for the access of multi-resolution datasets for volume rendering without decimation by using low pass filtering to get the best representation of the data at the lower scale. This both decreases processing time and improves image quality even during real-time image manipulation. Also, segmentation driven VOI visualization as well as location driven VOI visualization can be performed in a processing and memory efficient manner using the data format of the IWMF. Therefore, by using IWMF, volume rendering is interactive and practical, allowing processing solely for display purposes. Because of the way the data is packed, lower resolution processing is possible by retrieving the data directly from the desired resolution level or levels.

Volume rendering is currently used to process volume data from CT imaging systems 50, which produce three-dimensional stacks of parallel plane images, each of which consist of an array of X-ray absorption coefficients. Typically, CT images have a resolution of 512*512*12 bits, with up to 500 slices in a stack. In the 2D domain, these slices can be viewed one at a time. The advantage of CT images over conventional X-ray images is that the CT images contain information from a single plane. A conventional X-ray image, on the other hand, contains information from all of the planes, resulting in an accumulation of shadows that are a function of the density of anything that absorbs the X-rays, such as tissue, bone, and organs.

There are a number of different methods used for volume visualization, such as Rendering voxels in binary partitioned space, Marching cubes, and Ray casting. In Rendering voxels in binary partitioned space, choices are made for the entire voxel. Unfortunately, this can produce a "blocky" image. It also has a lack of dynamic range in the computed surface normals, which produces images with relatively poor shading.

The marching cubes approach solves the aforementioned problem, but causes other problems. The biggest disadvantage is that marching cubes requires that a binary decision be made on the position of the intermediate surface that is extracted and rendered. Also, extracting an intermediate structure can cause false positives (artifacts that do not exist) and false negatives (discarding small or poorly defined features).

Ray casting allows the best use of the 3D data and does not attempt to impose any geometric structure on 3D data. Ray casting solves one of the most important limitations of surface extraction techniques, namely the way in which a projection of a thin shell in the acquisition space is displayed. Surface extraction techniques fail to take into account that, particularly in medical imaging, data may originate from fluid and other materials, which may be partially transparent and should be modeled as such. Ray casting does not suffer from this limitation.

Another functional domain of Workflow Applications is Archive/Retrieval 242, which improves the ability of the Technologist to access just the portion of data at the desired resolution level that they wish to operate upon. File Format and Compression for three or more dimensions as explained before with regards to FIG. 7. Region of interest access can be in 2D (a portion of a large image), 2D plus time (functional attribute pertaining to a 2D region, such as blood flow through a vein in one plane), 3D (a subset of the whole volume of data), 3D plus time (functional attribute of a volumetric region, such as contrast/metabolic uptake in a volume of a tumor), or multi-spectral, multi-phasic and multi-tracer datasets.

Connectivity 248 is the next functional domain in the matrix 200. In the past, DICOM had stored header information for each slice of every image. With the DICOM multi-frame standard format, one global file header comprises all of the needed header information and the multiple images are stored in raw data format. By combining the IWMF with the DICOM multi-frame format, the file format of the IWMF framework can utilize the existing DICOM multi-frame standard and communicate to other devices, such as other imaging systems, using the file format described previously. In addition, the multi-dimensional data in the IWMF format is arranged such that the smallest resolution data is always the first to be accessed. This allows for perceptually gradual decoding of the data to higher (larger) resolutions without the user or algorithm component having to wait for the availability of the full data The next functional domain is Beyond 3D 254, comprising such Workflow Applications as Dynamic 3D Motion, Multi-Spectra, Multi-Tracers, and Multi-Phase. The IWMF format is easily extendable to represent Dynamic 3D motion, or volumetric data taken over time in a multi-phase format, e.g. respiratory gated CT images, brain perfusion images, cardiac images, and the like. Visualization of volumetric data over time or over anatomical cycles involves processing and displaying a huge amount of data, which is beyond current computer capabilities. Decimation of the data into smaller sets requires processing multiple volumes and is not conducive to real-time visualization. However, the IWMF provides a format for access of sub-resolution data without the need for real-time processing that makes it possible to interactively visualize such datasets. Therefore, 3D data processing using IWMF can easily be extended to dimensions beyond 3D. As an additional example, with real-time, 3D acquisition systems (e.g., 4D ultrasound), dynamic anatomical motion can be represented using the IWMF format to improve the throughput and eliminate data bottleneck. Similarly, the IWMF format is extendable to multi-spectral data, e.g., dual-energy X-ray or CT imaging. Multi-Spectra imaging comprises multi-energy datasets which are acquired using different acquisition parameters, energy levels, and wavelengths, for example. In multi-spectral imaging, spatially correlated data at multiple energies is acquired and reconstructed to obtain decomposed images, such as soft-tissue and bone images. Therefore, the Technologist may choose to review only the spectra information of interest with a particular application. As another example, the IWMF framework can be extended to one or multiple tracer datasets acquired with one or multiple imaging modalities. For example, an application may acquire datasets of first, second and third tracers, but may only be interested in a specific ROI and how the tracers act within the ROI. The IWMF framework is also useful for Multi-phase studies. For example, a three phase liver study using contrast agent acquires three sets of 3D images, wherein sets may be acquired at the arterial phase, delayed arterial and portal/venus phases.

The IWMF framework is particularly well suited to multi-scale and single or multi-modality image registration problems (also applying to Registration in Analysis 224 ). Instead of needing to first build the hierarchy, the framework data format allows for a direct hierarchical registration approach that can enable coarse to fine registration depending on the users purpose. Registration may be implemented using a multi-scale, multi-region, pyramidal approach. In this approach, a different cost function highlighting changes may be optimized at every scale. Such cost functions can be correlation methods, such as mathematical correlation and sign-change measurement, or statistical methods such as entropy measurements and mutual information. Images are re-sampled at a given scale and then divided into multiple regions. Separate shift vectors are calculated for different regions. Shift vectors are interpolated to produce a smooth shift transformation, which is applied to warp one of the images. The images are re-sampled and the warped registration process is repeated at the next higher scale until the pre-determined final scale is reached.

Figure 10:
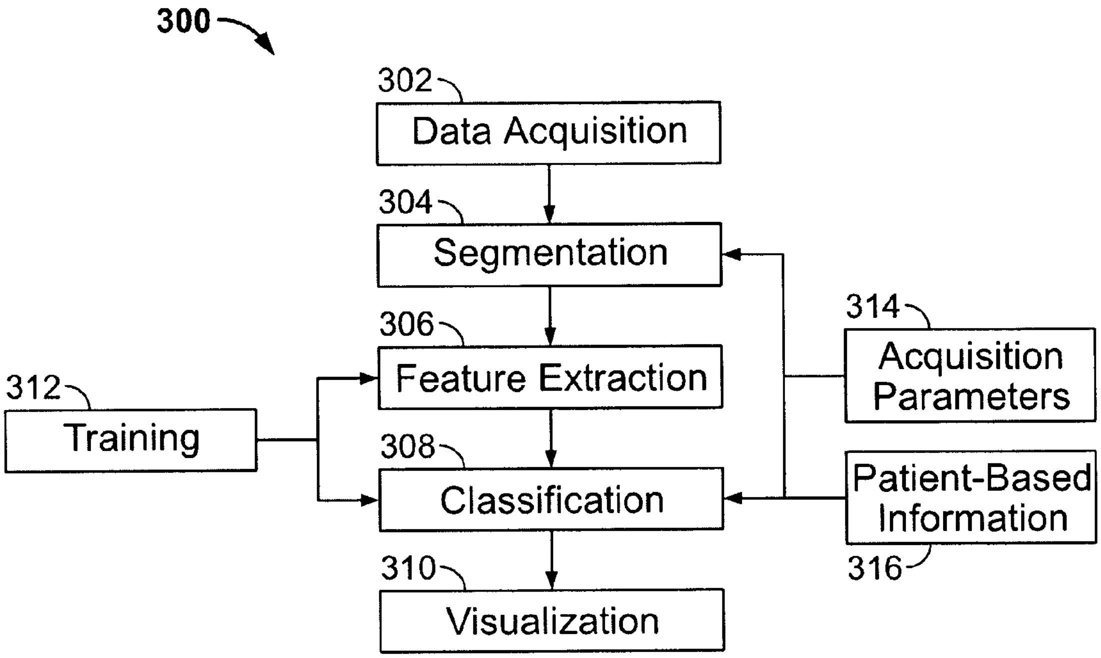
FIG. 10 illustrates a CAD process in accordance with an embodiment of the present invention.

The following provides additional information for the CAD Workflow Applications. FIG. 10 illustrates a flow chart of a CAD process 300 in accordance with an embodiment of the present invention. CAD previously had the complication of an inherent scale space dimension, e.g. finding spherical nodules in the lung may require the detection algorithm to detect features at a range of scale from 2 mm to 30 mm. Typically, prior art algorithms worked at various scales by either changing the feature detection component or by sub-sampling the data to accomplish detection of features over a range of scales. With IWMF, the data is already transformed and stored in a format that allows direct access to different scales for the detection component of the CAD algorithm, speeding up the entire CAD algorithm.

In step 302, CAD can use acquired data from a combination of one or more of the following sources: image acquisition system information from a tomographic data source, diagnostic tomographic data (e.g. raw data in projection or Radon domain, single or multiple reconstructed 2D images ("slices" of the patient) of a 3 D reconstructed volumetric image data set, and non-image information databases (e.g. patient history)). It should be understood that other data sources may be used.

Figure 11:
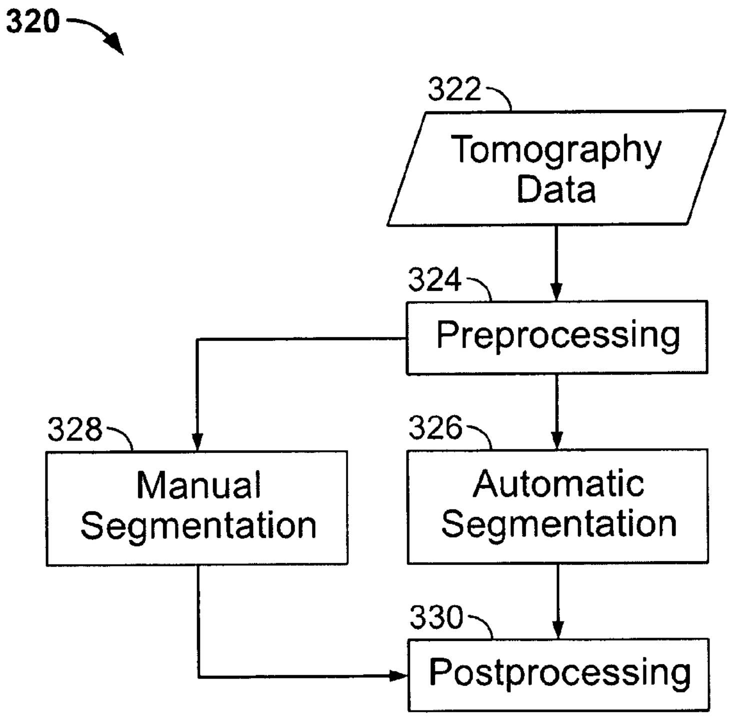
FIG. 11 illustrates a flow chart of a segmentation process for data in accordance with an embodiment of the present invention.

Segmentation (step 304 ) is further discussed in FIG. 11. FIG. 11 illustrates a flow chart of a segmentation process 320 for data in accordance with an embodiment of the present invention. Segmentation may be defined as the process of defining a part or all of the data to be operated upon. In step 322, tomography data is received or accessed. This may be accomplished by the computer 68 of the CT imaging system 50 or by a processing system, such as the computer 12. In step 324, preprocessing of the data is accomplished.

For example, with segmentation, a region of interest (ROI) can be defined to calculate features in the tomographic data. The ROI can be defined in several ways, such as using the entire dataset or using a part of the data, such as a candidate region within a specific region. Several techniques or combinations of techniques could be used for this purpose including, but not limited to, iterative thresholding, k-means segmentation, edge detection, edge linking, curve fitting, curve smoothing, 2D/3D morphological filtering, region growing, fuzzy clustering, image/volume measurements, heuristics, knowledge-based rules, decision trees, and neural networks.

The segmentation of an ROI may be performed manually (step 328 ) and/or automatically (step 326 ). With manual segmentation, the Technologist selects a protocol designed to display the data at one or more predefined resolution levels. The user then delineates the ROI using a mouse or any other suitable interface (e.g. touch screen, eye-tracking, voice commands). With automated segmentation, an algorithm can use prior knowledge such as the shape and size of a mass to automatically delineate the ROI. The prior knowledge may be input by the Technologist based on a previous scan and may be stored in patient identification data. In addition, a semi-automated method which is the combination of the steps 326 and 328 may be used. Once the segmentation is complete, in step 330 the computer 68 completes post-processing, as desired.

Returning to FIG. 10, in steps 314 and 316, acquisition parameters and patient-based information may be incorporated into the segmentation processing of step 304. Examples of acquisition parameters are kVp and dose, and examples of patient based information may be age, gender, smoking history, family history for the propensity of a disease, and the like.

Prior to feature extraction in step 306 and classification in step 308, prior knowledge from training is incorporated in step 312. The training phase involves the computation of several candidate features on known samples of normal and abnormal lesions. A feature selection algorithm is then employed to sort through the candidate features and select only the useful ones and remove those that provide no information or redundant information. This decision is based on classification results with different combinations of candidate features. The feature selection algorithm is also used to reduce the dimensionality from a practical standpoint, as the computation time would be enormous if the number of features to compute is large. Thus, a feature set is derived that can optimally discriminate normal lesion from abnormal lesion. This optimal feature set is extracted on the regions of interest in the CAD system. Optimal feature selection can be performed using a well-known distance measure including divergence measure, Bhattacharya distance, Mahalanobis distance, and the like.

Figure 12:
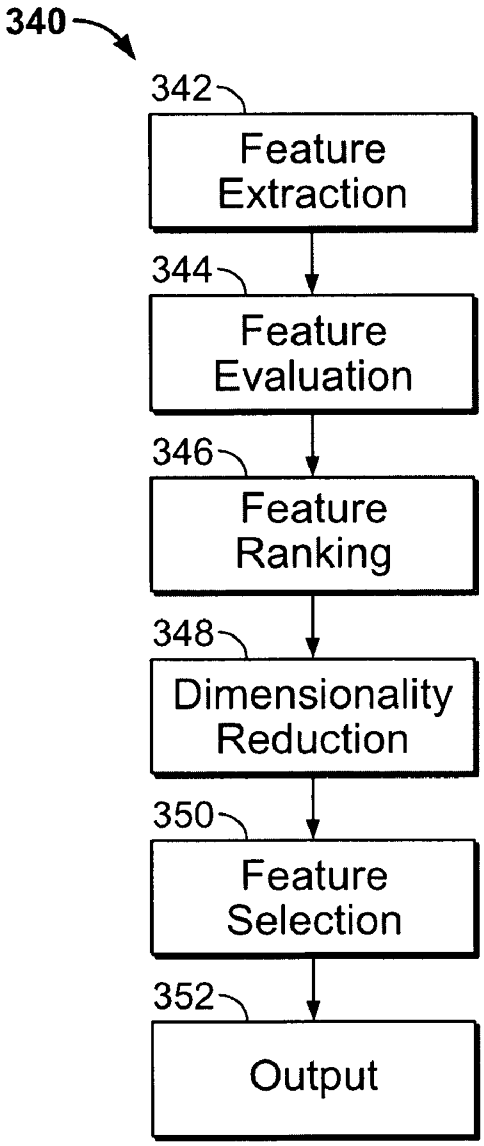
FIG. 12 illustrates a feature extraction process in accordance with an embodiment of the present invention.

Returning to step 306, FIG. 12 illustrates a flow chart of a feature extraction process 340 in accordance with an embodiment of the present invention. In FIG. 12, computations are performed on the data sources.

In step 342, multiple feature measures may be extracted from image-based data, such as from tomography images, using ROI statistics such as shape, size, texture, intensity, gradient, edge strength, location, proximity, histogram, symmetry, eccentricity, orientation, boundaries, moments, fractal dimensions, entropy, and the like. For projection space data, features such as location, shape, or size of feature projection in a view or location consistency from view-to-view may be extracted from the dataset. On acquisition-based and patient-based data, the data themselves may serve as the features, such as patient history (e.g. age, gender, smoking history), and acquisition data (e.g., kVp, dose).

In step 344, the features extracted in step 342 are evaluated in terms of the ability to separate the different classification groups using known distance criteria such as Divergence, Bhattacharya distance, and Mahalanobis distance. In step 346, the features are ranked based on the distance criteria. In step 348, dimensionality reduction is accomplished by eliminating correlated features. In step 350, the highest ranked feature is selected and features are added to it (based on a descending ranking) until the performance no longer improves. In step 352, the optimal set of features is output.

Figure 13:
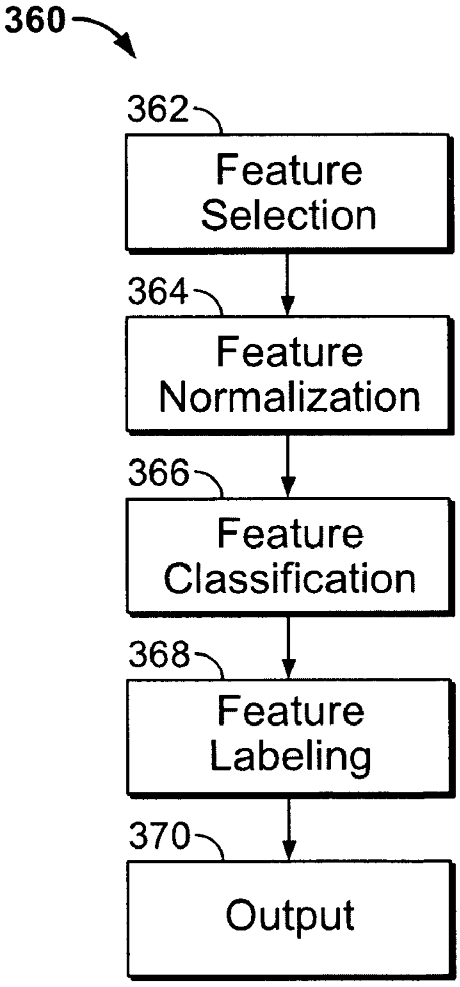
FIG. 13 illustrates a pre-trained classification algorithm which may be used during the feature classification process in accordance with an embodiment of the present invention.

Returning to FIG. 10, flow passes to step 308 for feature classification. As discussed previously in steps 314 and 316, one or more acquisition parameters and patient-based information may be incorporated within the feature classification. FIG. 13 illustrates a flow chart of a pre-trained classification algorithm 360 which may be used during the feature classification process in accordance with an embodiment of the present invention. The steps of FIG. 13 are used to categorize one or more features or ROIs into normal and abnormal lesions.

In step 362, features are selected by applying multiple relevant feature measures from tomography images to the data at the appropriate resolution level. Measures may be shape, size, texture, intensity, gradient, edge strength, location, proximity, histogram, symmetry, eccentricity, orientation, boundaries, moments, fractal dimensions, entropy, and the like.

In step 364, the feature measures are normalized with respect to feature measures derived from a database of known normal and abnormal cases of interest, such as by incorporating prior knowledge from training (step 312 of FIG. 10). In step 366, the features are classified using known prior art methods. Decision tree analysis, discriminant function analysis, Bayesian classifiers, Bayes' minimum-risk method, clustering techniques, similarity measure approach, neural networks, rule-based methods, fuzzy logic and the like can be used for classification.

In step 368, the features and/or feature clusters are labeled. Following the identification and classification of a suspicious candidate lesion, its location and characteristics must be displayed to the reviewer of the data. In certain CAD applications this is done through the superposition of a marker (e.g. arrow or circle) near or around the suspicious lesion. In other cases CAD affords the ability to display computer detected (and possibly diagnosed) markers on any of the multiple data. In this way, the reviewer may view only a single data upon which results from an array of CAD operations can be superimposed (defined by a unique segmentation (ROI), feature extraction, and classification procedure) resulting in a unique marker style (e.g. different color). In step 370, a labeled output is provided.

Flow returns to FIG. 10 and step 310 for visualization of the data. For example, the tomography image data may be reviewed by human or machine observers. CAD techniques could operate on one or all of the data, and display the results on each kind of data, or synthesize the results for display onto a single data. This would provide the benefit of improving CAD performance by simplifying the segmentation process, while not increasing the quantity or type of data to be reviewed.

It should be understood that CAD can be performed once by incorporating features from all data or can be performed in parallel. The parallel operation would involve performing CAD operations individually on each data and combining the results of all CAD operations (AND, OR operation or a combination of both). In addition, CAD operations to detect multiple diseases can be performed in series or parallel.

While the invention has been described in terms of various specific embodiments, those skilled in the art will recognize that the invention can be practiced with modification within the spirit and scope of the claims.

What is claimed is:

1. A method for handling data, comprising:

decomposing data into a plurality of resolution levels using an integer wavelet decomposition;

compiling a data stream comprising said plurality of resolution levels in a predetermined order;

accessing only one resolution level of said plurality of resolution levels associated with a workflow application; and performing said workflow application on said only one resolution level.

2. The method of claim 1, further comprising:

identifying an item of interest within said data at said only one resolution level;

identifying a data block representative of said item of interest; and accessing said data block to perform a workflow application.

3. The method of claim 1, said workflow application pertaining to a functional domain of one of acquisition, processing, analysis, display, archive/retrieval, connectivity, and beyond 3D.

4. The method of claim 3, wherein said workflow application for said acquisition functional domain is one of Quick Preview, Quality Control, CAD, Artifact Reduction, and Acquisition Speed up.

5. The method of claim 3, wherein said workflow application for said processing functional domain is one of Noise Reduction, Artifact Reduction, Image Enhancement, Image Reconstruction, and Storage of unprocessed data for future processing.

6. The method of claim 3, wherein said workflow application for said analysis functional domain is one of Computer-Aided Detection, Segmentation, Computer-Aided Diagnosis, Pattern Recognition, and Registration.

7. The method of claim 3, wherein said workflow application for said display functional domain is one of Volume Rendering, Volume of Interest Rendering, and Computer-Aided Detection results referencing.

8. The method of claim 7, further comprising:
accessing said only one resolution level;
processing said only one resolution level with at least one said workflow application of said display functional domain to form a three-dimensional image; and
displaying said three-dimensional image on a display.

9. The method of claim 3, wherein said workflow application for said archive/retrieval functional domain is one of File Format for three or more dimensions, Compression for three or more dimensions, and Region of Interest access.

10. The method of claim 3, wherein said workflow application for said connectivity functional domain is one of DICOM Multiframe and Rearrangement of Data.

11. The method of claim 3, wherein said workflow application for said Beyond 3D functional domain is one of Dynamic 3D motion, Multi-Spectra, Multi-Tracers, and Multi-phase.

12. The method of claim 1, said workflow application accessing a sub-resolution level, said workflow application forming one of a Quick Preview image representative of an image created using a higher resolution level and a Quality Control image for verifying at least one of acquisition parameters and content of said data.

13. The method of claim 1, further comprising:
acquiring said data with a Computed Tomography (CT) imaging system having a slip ring for transferring image data; and
performing said decomposing and acquiring steps substantially simultaneously to reduce bandwidth of said image data being transferred by said slip ring.

14. The method of claim 1, further comprising:
processing said only one resolution level with segmentation-based filters to reduce noise; and
forming an image having reduced noise based on a result of said processing step.

15. The method of claim 1, further comprising:
identifying a portion of said only one resolution level; and
analyzing said portion with said workflow application wherein said workflow application being one of Computer-Aided Detection, Computer-Aided Diagnosis, segmentation and pattern recognition.

16. The method of claim 1, further comprising:
identifying a region of interest (ROI) within said data, said ROI comprising one of two dimensions of image data overtime, three dimensions of image data, three dimensions of image data over time, and image data representative of multiple energy levels; and
identifying at least one data block within said data stream comprising said ROI at said only one resolution level, said performing step further comprising said workflow application operating on said at least one data block.

17. The method of claim 1, said compiling step further comprising forming a header comprising information related to each said plurality of resolution levels, said information identifying at least one of a number of resolution levels, row and column values for each said resolution level, and a compressed size of each of said resolution level.

18. The method of claim 1, said compiling step further comprising forming a header comprising information about each said plurality of resolution levels, said information comprising at least one of a version of a multi-resolution scheme used in said decomposing step and a type of integer wavelet forward transform used in said decomposing step.

19. A system for handling image data, comprising:
a transform module for performing forward and inverse transformations on multi-dimensional data using integer wavelet transforms, said forward transformation producing a plurality of resolution levels;
a processor for compiling a data stream comprising said plurality of resolution levels in a predetermined order; and
a memory for storing said data stream, said processor accessing only one resolution level of said plurality of resolution levels based on a workflow application.

20. The system of claim 19, said processor further comprising compiling said data stream having a lowest resolution level at a first end and a highest resolution level at a second end.

21. The system of claim 19, further comprising:
said transform module performing said forward transformation on said multi-dimensional data to form a first level of decomposition;
said processor identifying a first data block within said first level of decomposition, said first data block comprising a subset of said multi-dimensional data; and
said transform module performing said forward transformation on said first data block to form a second level of decomposition.

22. The system of claim 19, said system further comprising a Computer Tomography (CT) system utilizing a slip ring for image data transfer, said transform module decomposing said multi-dimensional data prior to said slip ring.

23. A method for forming a multi-resolution framework of data, the method comprising:
decomposing data into multiple resolution levels using an integer wavelet decomposition, said data comprising at least three dimensions, each of said resolution levels comprising data blocks representative of a volume of data;
compiling a data stream comprising said data blocks arranged in an order based on said resolution level;
accessing a first set of data blocks within said data stream at only one resolution level, said only one resolution level being associated with a workflow application; and
performing said workflow application on said first set of data blocks.

24. The method of claim 23, further comprising:
receiving said data over a period of time; and
displaying images based on said only one resolution level during said period of time.

25. The method of claim 23, said data further comprising an anisotropic volume, the method further comprising, prior to said decomposing step, decomposing said anisotropic volume with said integer wavelet decomposition in at least one dimension to form an isotropic volume.

26. The method of claim 23, further comprising:

receiving said data over a period of time;

said decomposing step decomposing said data as said data is received; and performing said workflow application during said period of time.

27. The method of claim 23, wherein said data comprises first, second and third dimensions, said decomposing step further comprising:

successively decomposing said data in said first, second and third dimensions to form a first level of decomposition; and successively decomposing said first level of decomposition in said first, second and third dimensions to form a second level of decomposition.

28. The method of claim 1, further comprising:

accessing only another one resolution level of said plurality of resolution levels associated with a workflow application; and performing said workflow application on said only another one resolution level.

29. The method of claim 1, further comprising combining results of the workflow application performed on said only one resolution level and said only another one resolution level.

* * * * *